United States Patent
Gage et al.

(10) Patent No.: US 8,200,453 B2
(45) Date of Patent: Jun. 12, 2012

(54) WEIGHT MANAGEMENT SYSTEM USING ZERO-READOUT WEIGHT SENSOR DEVICE AND METHOD OF USING SAME

(75) Inventors: Dennis Gage, New York, NY (US); Alex M Adelson, Andes, NY (US)

(73) Assignee: Permanens LLC, New City, NY (US)

( * ) Notice: Subject to any disclaimer, the term of this patent is extended or adjusted under 35 U.S.C. 154(b) by 371 days.

(21) Appl. No.: 12/543,041

(22) Filed: Aug. 18, 2009

(65) Prior Publication Data

US 2010/0049471 A1 Feb. 25, 2010

Related U.S. Application Data

(60) Provisional application No. 61/189,818, filed on Aug. 22, 2008.

(51) Int. Cl.
*G06F 15/00* (2006.01)
*G01G 9/00* (2006.01)
(52) U.S. Cl. .......................... 702/173; 177/1
(58) Field of Classification Search .................. 702/173, 702/188; 177/1, 50
See application file for complete search history.

(56) References Cited

U.S. PATENT DOCUMENTS 6,956,175 B1 * 10/2005 Daly et al. ..................... 177/1
7,454,972 B2 * 11/2008 Heyman et al. ................ 73/597

\* cited by examiner

*Primary Examiner* — Bryan Bui
(74) *Attorney, Agent, or Firm* — Kirschstein, et al.

(57) ABSTRACT

A method of, and a system for, controlling, managing and maintaining a client's weight are performed by placing a weight sensor device in a location that is convenient to the client, periodically generating weight signals at the sensor device, providing a computer system remote from the location of the sensor device, storing information associated with the client at the computer system, using a wired or wireless connection to connect the sensor device to the computer system, receiving and processing the weight signals in accordance with weight maintenance algorithms at the computer system, and reviewing the processed data by a professional manager to monitor the client's progress. The weight sensor device is provided with no indicator of the client's weight. The client is prompted to step on and off the sensor device. There is no visual display or other indication at the sensor device to indicate the client's weight.

17 Claims, 2 Drawing Sheets

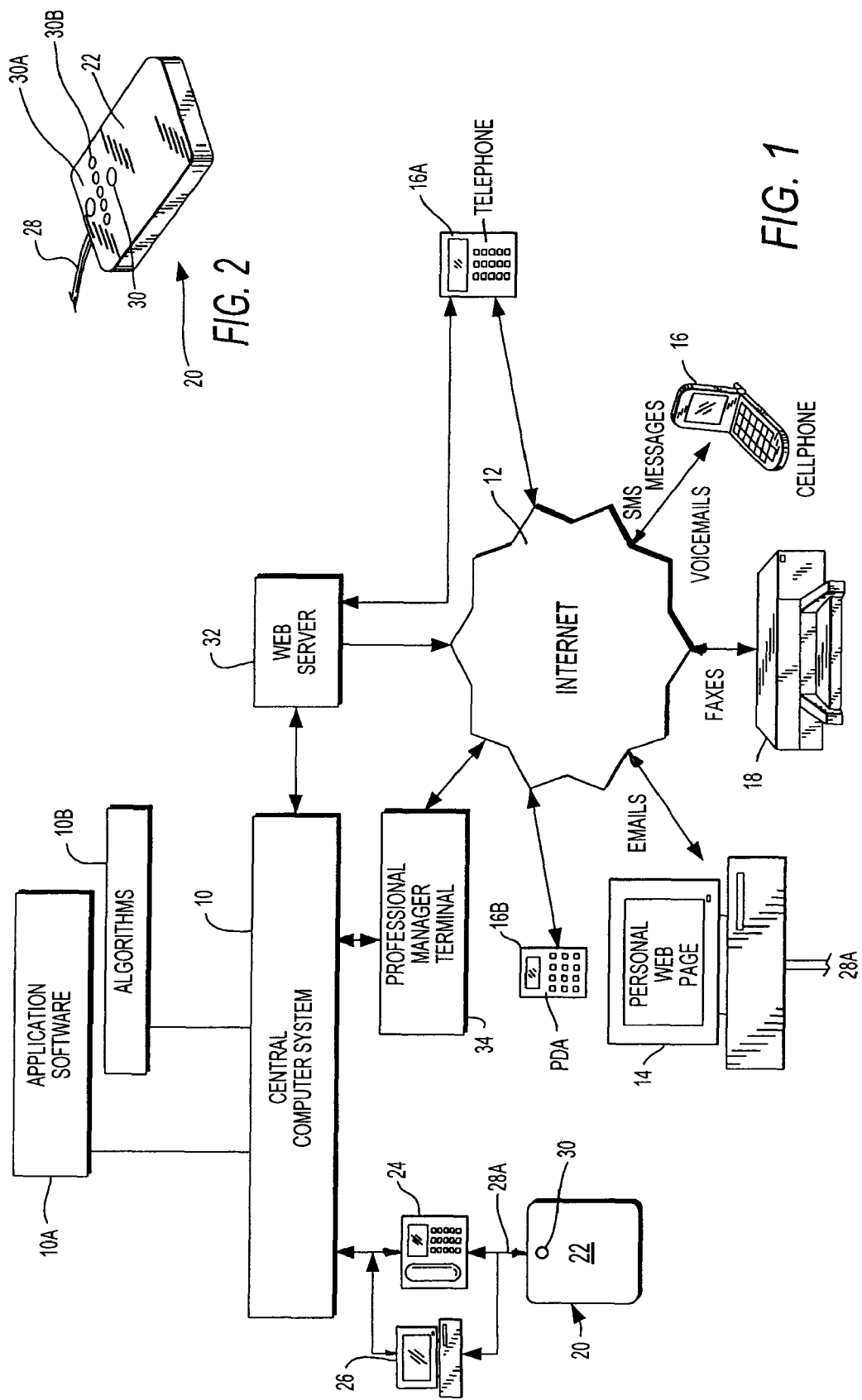

WEIGHT MANAGEMENT SYSTEM USING ZERO-READOUT WEIGHT SENSOR DEVICE AND METHOD OF USING SAME

CROSS REFERENCE TO RELATED APPLICATION

This application claims the priority of U.S. Provisional Patent Application Ser. No. 61/189,818, filed Aug. 22, 2008.

BACKGROUND OF THE INVENTION

The present invention generally relates to the field of human body weight management and to an improved system employing a zero-readout weight sensor device and method of using the same for controlling and managing body weight.

DESCRIPTION OF THE RELATED ART

Weight maladies persistently affect a significant population of the world. Whether that population is prosperous or poor, weight is a defining physical characteristic of the state of individual health. The aggregate effect for national populations is one of the significant forces contributing to their success or failure as a society. One can eat too many beans, as well too many hamburgers, with the same obesity result. In the western countries, in particular over the last hundred years of prosperity, the culinary villain has been too much meat and too many carbohydrates and sugar. Overweight has become a national health problem in these countries and a national epidemic creating terrible personal as well as economic costs to both individuals and governments. In the United States, the sad reality is that two-thirds of the population is overweight. This has led or will lead soon to a health cost approaching one fifth of the gross national product. It is an economic burden that most economic experts believe is unsustainable.

There exists a plethora of successful methods of reducing human body weight, but there is little known or available for permanently maintaining a weight once a weight reduction has been achieved. Weight reduction has been the subject of many studies and, as a result of some of these studies, effective methods of losing weight have evolved. Many of these methods have been well documented. Using a variety of the techniques disclosed by these studies, a significant group of the overweight population has successfully lost weight. The problem arises when considering the depressing statistics associated with weight permanence; that is, keeping the weight off permanently. It is well documented that approximately 85% to 90% of the population return to their original overweight condition within two years of having lost weight.

Weight management in the western countries, in particular in the United States, is a multi-billion dollar per year industry. There is a multitude of businesses including weight diet management services, diet food suppliers, gyms and exercise clubs, supplements, and other dietary products, as well as different equipment including weighing scales, to help individuals achieve their weight goals.

For example, one method of managing weight has been a personal program under the direction of a professional weight manager, very often a medical professional, e.g., a physician, a professional or physician's assistant, a physical therapist, etc., or a licensed professional, e.g., a physical trainer, a nutritionist, etc. However, one problem with this method is the time and cost required for a client or patient to travel to the location of the manager and be interviewed, weighed and advised. This problem is aggravated if the client has to travel a sizeable distance to meet with the manager. Sometimes, it is simply not convenient or practical, or in some cases, impossible for the client to travel to the manager. Sometimes, it is not convenient or practical for the manager to see the client as a result of other time and obligation responsibilities. These problems often discourage a client from visiting the manager when he or she most needs to be seen. Once a client begins to skip visits, the client often loses interest in the entire program.

Slimming club programs are another popular method of controlling and shedding a member's weight. A slimming club normally consists of supervised periodic group sessions, each typically lasting one to two hours. At these sessions, each member has his or her weight publicly measured and recorded, typically called a "weigh-in", and the member who has lost weight typically receives praise, while those that did not lose weight typically receive encouragement and support. Problems with this method include the embarrassment of a public weigh-in, as well as the time required for the member to travel to the location of the slimming club, and to be weighed and advised.

Rather than employing a professional manager or a slimming club, many individuals prefer to self-administer a weight management program by diet and exercise. Yet, the lack of oversight by another party often ends in failure.

All of these programs involve the use of weighing scales, which indicate a user's current body weight. Typically, the weight is displayed in numerical units on a visual display. However, it is well known that many people, especially dieters, do not wish to know their actual weight, or do not wish others to know their actual weight, because, to do so, would cause public embarrassment and humiliation, and have an undesirable psychological effect on them. These people simply do not wish to view or know their weight. Standing on a scale and seeing their actual weight reported to themselves or other parties is traumatic for much of the population. This is sometimes referred to as "scalitis". These are people who find the experience of the weighing process with its immediate weight indication report so unpleasant that they avoid or flat out will not do it. This is generally tied in with conventional human inclination of denial along with the mental anguish of failure.

The art has proposed scales with non-numerical readouts, for example, by displaying a green color if the weight is within a predetermined range and a red color if the weight is outside the predetermined range. However, here again, the use of colors still advises the user whether he or she has gained or lost weight and the approximate magnitude of that gain or loss. Many users, especially long-term dieters, wish to be shielded from this "softer" information; some users choose ignorance. The psychology of humans and their weight can be baffling considering how important weight is to one's self-image and good health. Years of multiple studies from different independent sources concerning this subject reaffirm these conclusions.

SUMMARY OF THE INVENTION

Experience indicates that an automated system that keeps a weight client in daily contact with a professional weight manager, either directly or remotely, is one of the methods that can provide a successful weight management solution for a significant number of the weight client population. In accordance with one aspect of this invention, a zero read-out weight sensor device serves as an integral component that provides the means for daily remote monitoring and interaction services at a low cost for the weight client.

The system is specifically styled and tailored by the professional manager, in collaboration with the weight client, for the specific needs and style that both agree will be best for the client. The system is unique because it provides, based on certain proprietary algorithms, the means for tracking daily weight variations and trends against a given weight client's history, metrics, and needs. The system provides the means for determining what is significantly happening to that client's weight before it would normally be noticed and/or responded to along with a personalized daily report. The system automatically communicates with the professional manager, and in turn responds with computed messages using one or a plurality of algorithms that utilize the client's database and employ the client's preferred communication style. Under certain circumstances, that leads to a decision by the professional manager that a manual, as opposed to an automatic, response is appropriate, and such response is easily implemented by the professional manager through the system.

The greatest value for the client is that he or she is being monitored and managed by a professional manager on a daily basis. The client is never alone in this process. The communication and analytical process is automatic (and manual where appropriate), constant, and tailored to the style desired by each client. Fundamental to the success of a given client is the style of communication; therefore, it is his or her preferred and most comfortable means of engagement.

The system is so designed that it provides the means for significant personalization—unique for each client—for the purpose of overcoming the normal resistance factors of human behavior and the common methods associated with systems that have been designed for the population at large.

The present invention therefore relates, briefly stated, to a method of, and a system for, controlling and maintaining a client's weight by placing the weight sensor device in a location that is convenient to the client, such as in the client's home, gym, workplace, etc., or by carrying the weight sensor device to a convenient location, such as a hotel. In other words, the location of the sensor device is placed where it is most convenient for the client to use.

The sensor device generates weight-related data signals from and transmits the weight-related data signals, either directly or wirelessly, to a communications device, such as a computer, personal digital assistant (PDA), cell phone, smartphone, or equivalent device, which in turn sends the data over the Internet to a central computer system; or conversely, a cell phone is wirelessly connected directly to the central computer system; or in still another method, a conventional telephone is used to transmit the data to the central computer system. The central computer system is remotely located from the sensor device. The data signals are received, stored permanently, and processed in accordance with the proprietary weight algorithms that are responsible for management and maintenance, and the processed data is sent to the professional manager who monitors the client's daily or incremental progress. Depending on the nature of the processed data, the level of and nature of the client's weight behavior, and the managing professional's appraisal, messages are either automatically or manually created and sent to the client.

The weight sensor device is provided with no indicator of the client's weight. In the most common embodiment of the invention, the client taps the sensor device with his or her foot or other convenient appendage, thereby initiating the weighing process. The client then waits for a signal by looking, listening, or feeling, indicating that the sensor device has been actuated to its "on" state, and therefore is ready to make a measurement. Once the readiness signal has been successfully received by the client, the client steps on the sensor device with both feet so that the client's full weight is being measured by the sensor device. Thereupon, a signal is generated that a successful weight measurement has been accomplished and recorded. Then, the client is free to step off the sensor device, and the sensor device cycles to the "off" state, thereby indicating such with a parting (or ending) signal.

However, in contrast to the prior art, there is no readout. There is no visual display or anything else to indicate, either directly or indirectly, the client's weight. Nor is any other significant information regarding the client displayed except, in some embodiments, the client's identity or equivalent. This generally applies to an embodiment of the sensor device that is to be used by multiple clients at a common location, such as a family group or health club, or equivalent. The client never receives at the sensor device any potentially distracting or unfavorable information. Therefore, the anxiety, psychological response, and other personal negative reactions, which are commonly associated with "weighing in", are, for the most part, mitigated.

Another aspect of the present invention resides in whether or not an automatic responsive communication (signal/message) from the central computer system is to be sent to the client with no need for any further consultation with the professional manager. In other words, the communication might indicate that the client is in his or her "safe zone" and requires no other management. The decision regarding sending the message is first "considered"—measurements based on all the personal data and time-based recorded data—by the algorithms in the central computer system and reported to the professional manager, and, if appropriate, simultaneously sent to the client. Messages will only be created in the style that has been designed and agreed to by the client in collaboration with the professional manager.

The professional manager can also choose from a variety of preprogrammed responses, or can manually create a response. After the manager has made the choice, the response is sent to the central computer system, recorded, dated, placed in the appropriate data file, and, in most cases, sent to the client. The system also accommodates special data that can be manually entered into the client's data file.

The response can be sent as an HTML, XML, or equivalent modality script and displayed directly on a monitor of a computer running a web browser, or an e-mail client. This response can be transmitted, over a wired or wireless link, to a communications signal receiving device operated by the client. Typically, this would be a home computer, a personal digital assistant (PDA), a cell phone, a smartphone, or equivalent. In cases where this is not possible, or convenient, the response can be sent via a telephone call, a short personal note through the mail, and/or by fax. The method and system embodying the present invention is thus able to permit the client to remain at home, at work, or at some other convenient location.

The client's reactions to the form and style of the automatic or manual professional response, the form and style of which was previously agreed to by the client in collaboration with the manager, reduces or mitigates unwanted psychological reactions, embarrassments, and/or distractions which interfere with positive outcomes. The client benefits from a style of communication and interaction he or she is most comfortable with, as well as the extremely important daily contact with the system and the knowledge that the manager is monitoring the client on a daily basis (with the exception of weekends in many cases).

The manager, or an appropriate surrogate, on a daily basis monitors all the clients under their management by examining a "cockpit view" of all the clients on a computer monitor, printout, or appropriate communication means.

In a preferred embodiment, this appears as a bar graph with each individual client identified with his or her unique number and an associated bar appearing in an aggregated stacked view that begins with a green color, and can go to a yellow color, and finally to a red color. Green, or another color, indicates that the client is within their "safe zone" (normal weight specification). Yellow, or another different color, indicates that the client is approaching and about to exceed their "safe" zone. Red, or yet another different color, indicates that the client has exceeded their "safe zone". Instead of colors, different textures can be substituted or shades of one color can be used, or a variety of graphical symbols, etc.

The manager can "point and click" on the bar graph and "drill down" to a complete view of all the client data (records). The manager can review the data associated with the client at any time and communicate with the client when it is most convenient for both parties.

The "cockpit view" is employed as an extremely efficient and low cost method for the manager to observe and manage a large group of people. It provides the means for quick and easy decision-making and enables the manager with the ability to quickly respond to those who are in need of quick assistance. It engenders the feeling of intimacy, confidence, and responsibility in the relationship between the manager and each of his or her clients.

To further the efficiency of the method, and therefore keeping costs down, the daily communication message between the professional manager and a given client, when that client is in their "safe zone", is automated even though the client is being monitored by the manager. These are the daily communication "state-of-the-client" messages, which can vary anywhere from the exact weight of the daily weight measurement, a smiling or frowning face emoticon, a color code, a text message, or to no communication whatsoever which, in itself, is a virtual communication. If there are problems or the beginning of problems, then a reminder or suggestion concerning a positive counteraction, or the need to check in with the manager, or make an appointment for a meeting with the manager, can be sent to the client.

The system includes positive encouragement messages and/or positive suggestions and a variety of knowledge database messages to continuously raise awareness of information that is revealing, useful, and helpful to the client in successfully managing his or her weight state over time. The more knowledge and encouragement the client receives, the higher are the chances for success. The system provides an option for comparing the client's progress against the average peer progress in the form of a percentile report. This is a technique for helping very competitive personalities.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a schematic showing the overall system and the method embodying the present invention;

FIG. 2 is a perspective view of a weight sensor device used in the system and method embodying the present invention.

DETAILED DESCRIPTION OF THE PREFERRED EMBODIMENTS

Figure 3:
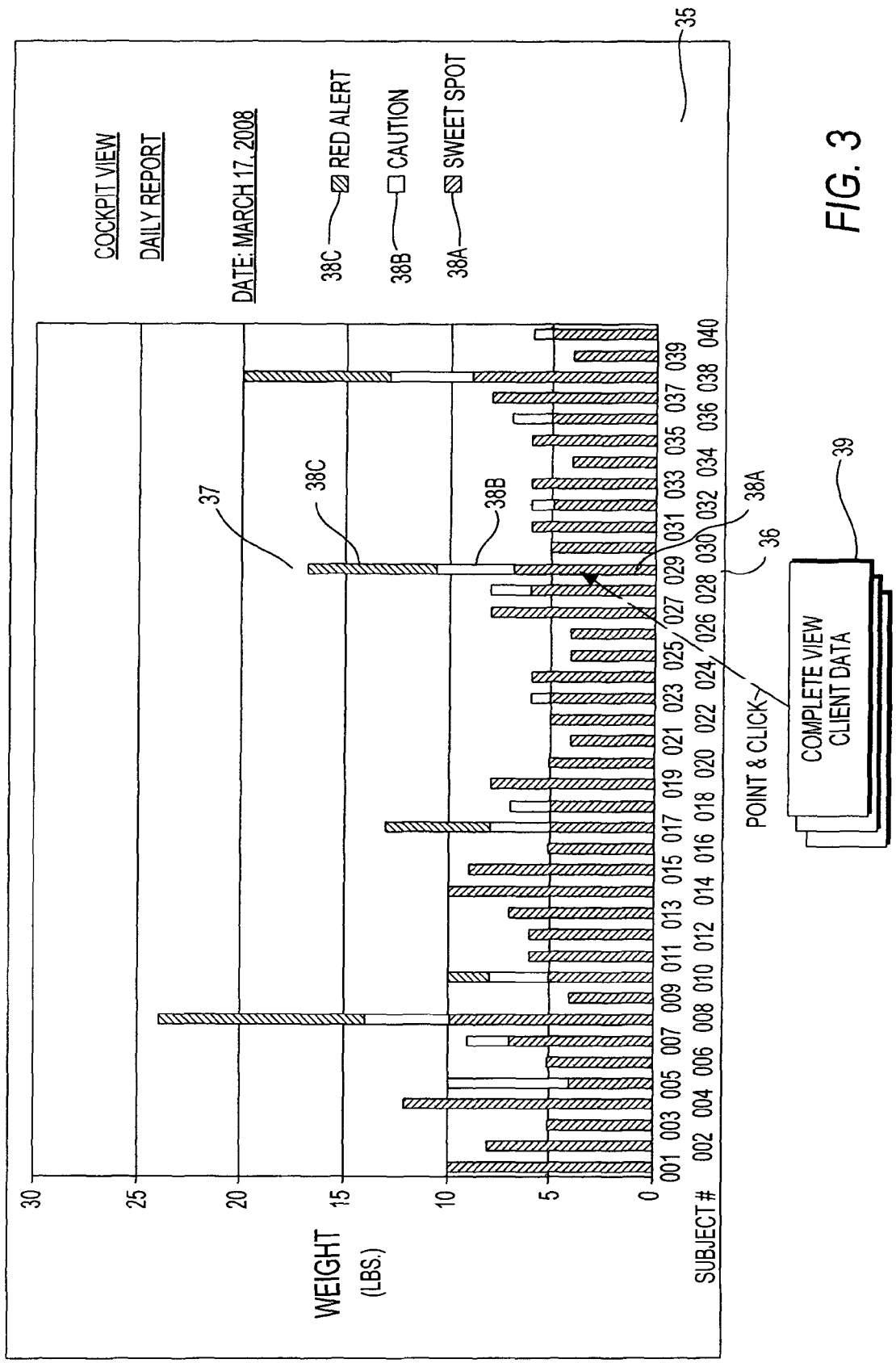
FIG. 3 is a "cockpit view" on a display showing daily reports of each professional manager's client base in accordance with the present invention.

Referring now to FIG. 1 of the drawings, certain personal data is initially recorded for a new client in a central computer system 10 through a professional manager terminal 34, typically by having the client processed at the offices of a professional manager, by the professional manager, surrogate, or equivalent. Such personal data may include, but are not limited to, predetermined specific details including his or her current weight, current body fat index, weight goals, gastric dispensability, desired weight loss and/or weight zone to be maintained, desired weigh-in frequency, demographic data, personal history data, family history data, vacation dates, contact data, credit data, and any other data that the manager wants to use in managing the client.

The next step involves personal preference data, which includes the choice of communication style, method, and timing. Each individual client, in collaboration with the professional manager, will choose the client's preferred form of communication from a menu of form and communication styles. These choices may include, for some personalities, exact information such as all data reported precisely in text form in real-time. Another personality may choose icons indicating the general state of their weight conditions on an "every-other-day" report. Yet another personality may choose both graphical and text reporting in a flowery and positive style. There are also personalities who will elect to have no daily reporting whatsoever unless they are not being successful. The variations are quite extensive and can, as a client progresses through the system, be adjusted to suit the circumstances and level of success.

This data is also entered into the file associated with a given client into the central computer system 10 through the professional manager terminal 34. Each professional manager, or managers in the case of group practices, will have access to the professional manager terminal 34 that will provide access only to a given manager's client data base, or in the case of multiple professional managers, that group's client data base. All data is subject to, and compliant with, HIPAA privacy compliance practices and requirements or equivalent regulatory practices and requirements associated with the geographic and/or political location of the professional management practice.

Another communication choice, or choices, that are made at the initialization are the client's communication modalities, which can include HTML, XML, or equivalent modality scripts that are displayed directly on a monitor of a communications device, such as a computer 14, running a web browser, or on a personal digital assistant (PDA) 16B, or on a cellular phone 16 which can include PDA capabilities thereby rendering it a smartphone, or on a conventional telephone with a display 16A, or on other equivalent devices and, alternately or simultaneously, an e-mail or e-mail attachment sent to a computer, such as the computer 14, or the phone 16, or other equivalent devices. There are other communication techniques and devices that can also serve to perform these functions, such as wireless phones through WANS, LANS (WiFi and/or Bluetooth), or standard wireless communication systems (3G, Bluetooth, etc.), voicemail, fax to facsimile machine 18, fax to computer 14, computer to facsimile machine 18, digital TV, regular landline, special or dedicated personal digital assistants (PDA), etc. Messages can also be in the form of SMS text messages, SMS picture messages, computer generated voicemails, avatars, etc., that are forwarded to a variety of destination communication devices 14, 16, 16A, 16B, and/or 18 or equivalents, as requested by the client as indicated in his or her initialization file. If the client has requested in his or her file that no messages are to be sent, or sent only under dire circumstances, then the application software 10A located in the central computer system 10 will comply.

The client also chooses, if desired, a back-up communication preference to be used if the first communication choice is unavailable or not working. All of these choices, assignments, and personal data reside in a personal client profile file located in, and processed by, the computer system 10.

Each client is assigned a unique identifier supplied by, or associated with, a weight sensor device 20, as described herein below. The identifier may be provided on a pre-printed label attached to the bottom of the sensor device 20, or a card or equivalent included with the sensor device 20. Alternately, a radio frequency identification (RFID) tag or transponder and/or a label bearing a bar code symbol, can be attached to the sensor device 20 for the same purpose.

In yet another form of the sensor device 20, a bar code symbol reader, an RFID reader, or a keyboard is included for the purpose of using the sensor device 20 for an unlimited number of clients. In this form, the sensor device 20 is not dedicated to a person or small group such as a family, but can be activated through the bar code reader, the RFID reader, or the keyboard that inputs to the system a specific unique identifier permitting and guiding weight data generated by the sensor device 20 to the appropriate file, or equivalent. Similarly, a communications device having a display can be associated with the sensor device 20, in which case a plurality of identifiers, e.g., icons, are visible on the display, and selection of one of such icons identifies the client.

As best seen in FIG. 2, the sensor device 20 consists of a housing with a platform 22 on which the client taps or steps on to initiate and turn on the sensor device in order for the client to be weighed. The sensor device has a built-in indicator 30 or indicators, typically light emitting diodes (LEDs), to indicate that the sensor device 20 is on and ready to make a measurement, and when a measurement is successfully taken, the indicator(s) signals the same. The same task could be accomplished with sound or vibrations.

In one embodiment, there are two indicators 30 and 30A. When the device 20 is first tapped or stepped upon, one 30 of the indicators turns on, indicating that the sensor device 20 has been turned on. When that indicator 30 starts to flash or blink, the sensor device 20 is indicating that it is ready to take a measurement; when a successful measurement has been made, the other indicator 30A flashes or blinks. Indicators 30 and 30A can emit different colors.

In an alternate embodiment, one LED or equivalent lighting source, with the ability to change colors, performs the same function as the indicators 30 and 30A. In another embodiment, a liquid crystal display (LCD), organic light emitting diode (OLED), or equivalent device can perform this function using text to announce the various "on-ready-measurement success" states.

In still another embodiment, an auditory signal can be used instead of, or supplementing, visual indicators. When the sensor device 20 is tapped, a steady auditory signal is emitted. When the sensor device 20 is ready for a measurement, the steady signal changes pitch (tone), becomes incremental, warbles, or some other obvious differentiator. When a successful measurement has been made, the auditory signal again changes to yet a different auditory signal.

In still another embodiment, different vibrations, each representing a different state of the process, which are meant to be felt (or detected) by the human body through appendage touching can also be employed.

The sensor device 20 may have a built-in electronic modem dialer or a transmitter for a connection through a WiFi, Bluetooth, or similar wireless protocol, or can be hard-wired by cable 28A to various communications devices, such as a telephone 24 connected to a home telephone line, a cell phone, a personal digital assistant (PDA), a smartphone, or a home tower or portable computer 26 connected to the Internet through a cable (TV, Internet, and/or VOIP service), or hard-wired telephone cable, satellite, or other wireless means.

The sensor device 20 may be battery-operated and include a battery compartment located on the underside of the device, or may be plugged into an AC or DC source such as a typical mains outlet or auxiliary power supply by a power cord 28.

The sensor device 20 has a load cell operatively connected to the platform 22, for measuring the client's body weight, and for generating an electrical weight signal indicative of the measured weight. The sensor device 20 has no readout. There is no visual display or any other means to indicate the client's weight or any other indication concerning the state of the client. As described above, the client cannot get any potentially distracting or unfavorable information from the sensor device 20, nor does the client learn his or her actual weight from the sensor device 20, which information can be counterproductive for some clients.

Upon the completion of a successful weight measurement, the modem dialer or transmitter automatically sends the electrical weight signal to the client's communications device or data station, which can be a personal computer, a PDA, a cell phone, a smartphone, or any device capable of transmitting the data to the central computer system 10. The modem dialer or transmitter is programmed to dial a prescribed telephone number or access a prescribed web address. It is simply the action of tapping or standing on the platform 22, receiving a signal that the sensor device is on and ready to measure weight, and then achieving a successful weight measurement that activates the transmission means for the weight data. In the case of the client's data station not being on or malfunctioning, the sensor device 20 will store the information for a later data upload when the client's data station is operable.

The client may transmit the data as often or as infrequently as he or she wishes although, preferably, the client should follow the preselected weigh-in frequency and weigh-in at the beginning of a metabolic day, as described below, before any food is consumed. The data received by the central computer system 10 is recorded in a central weight database, wherein a record has been created for each client, and each transmission is recorded together with the date/time that the data was received and recorded. The sensor device 20 can be used in the client's home or taken wherever there is access to a telephone or Internet connection or equivalent, e.g., at the office, on vacation, etc.

The central computer system 10 is connected to the Internet 12 via a web server 32 and/or equivalent, and can be located anywhere. The professional manager can also be located anywhere, e.g., in a clinic, a hospital, a doctor's office, a clinician's or nutritionist's office, gym, or the like, or even at the central computer system 10. It is only necessary for the professional manager or the manager's surrogates to have access to the terminal 34 that can access the central computer system 10. Thus, a single professional manager can service a multitude of clients who can be located near and far from the manager or the central computer system 10. The clients and the professional manager need not even be in the same state, or even in the same country for that matter. The only connection between the professional manager and a client is the Internet 12 and/or a telephone communications system or equivalent except when an office visit is appropriate.

The method of the present invention is further performed, at the central computer system 10, by receiving the weight signal sent from the weight sensor device 20 via the telephone/Internet connection or equivalent, and by making and keeping a record of the client's managed weight maintenance zone; this includes initial and current weight, weight goals, weigh-in frequency, demographic data, personal history, family history, vacation dates, contact or no-contact data, etc. and, if required, desired weight loss.

As part of the application software 10A located in the central computer 10, there are certain algorithms 10B that aid in the management and analysis of the client's weight state. These are sometimes referred to herein as the weight management algorithms 10B. They reside in the central computer system 10 and are used to interact with the individual client profile databases on a periodic or daily schedule. The algorithms 10B apply rules and analysis that aid in permanently maintaining the client's desired, reduced, or ideal weight.

Each day, or alternately at an agreed upon frequency, the weight management algorithms 10A and application software 10B are automatically used to review each client's record and aid in decisions affecting the future recommendations, activities, and other matters regarding the client's weight goals. As a consequence, a daily or periodic response is generated and sent via the professional manager terminal 34 to the client's communication devices 14, 18, 16, 16A and/or 16B. At this point, the algorithms 10B determine whether or not a responsive communication (signal/message) from the central computer system 10 is to be sent to the client with no need for any further consultation with the professional manager. In other words, the client is in his or her safe zone and requires no other management in the process.

The decision regarding sending the message is first weighed by the algorithms 10B in the central computer system 10 and reported to the manager through the professional manager terminal 34, and if appropriate, simultaneously sent to the client through the Internet 12, or hard line telephone 16A, or equivalent. Messages will only be created in the style that has been designed and agreed to by the client in collaboration with the professional manager.

If the client has not performed the agreed upon daily or periodic weigh-in, the system will begin sending reminder messages via previously agreed upon communication modalities.

If certain boundaries are exceeded, a message is first sent to the professional manager via the professional manager terminal 34 and not to the client where one of three choices is made by the manager. The first is to let the system automatically respond using the algorithms to control the response. Second, the manager can choose from a variety of preprogrammed responses. Third, the manager can create a response manually. After the manager has made the choice, the response is sent to the central computer system, recorded, dated, placed in the appropriate data file, and sent to the client.

The response can be sent as an HTML, XML, or equivalent modality script and displayed directly on a monitor of a communications device, such as a computer running a web browser, or as an e-mail attachment to the client's communication devices 14, 18, 16, and/or 16B. In cases where this is not possible, or convenient, the response can be transmitted as a call via the telephone 16A, or even a short personal note through the mail. The method and system embodying the present invention is thus able to permit the client to remain at home or at some other convenient location.

The professional manager, or an appropriate surrogate, on a daily basis monitors all the clients under management by examining a "cockpit view" of a group of the clients on a monitor. As shown in FIG. 3, the cockpit view appears as a bar graph 35 with each individual client identified with his or her unique number 36 and an associated bar appearing in an aggregated stacked bar 37 that begins with a green colored area 38A, that can go to a yellow colored area 38B, and finally can go to a red colored area 38C, or another appropriate series of different colors.

Green, or the first color in the stacked series, indicates that the client is within his or her "safe zone" (normal weight specification). Yellow, or the next color in the series, indicates that the client is approaching and is about to exceed his or her "safe" zone. Red, or the next color, indicates that the client has exceeded his or her "safe zone". Colors can be substituted with shades of gray, textures, icons, etc.

The professional manager can "point and click" on the bar graph and "drill down" to a complete view of all the client data (records) 39. The professional manager can review the data associated with the client at any time and communicate with the client when it is most convenient for both parties. Furthermore, much of the communication from the professional manager is automated such as the daily communication "state-of-the-client" message, which can vary anywhere from the exact weight of the daily weight measurement, a smiling or frowning face emoticon, a color code, a text message, or to no communication whatsoever, which in itself is a meaningful communication. If there are problems or the beginning of problems, then a reminder or suggestion concerning a positive counteraction, or the need to check in with the manager or make an appointment for a meeting with the manager, may be made.

The system includes positive encouragement messages and/or positive suggestions and a variety of knowledge database messages to continuously raise awareness of information that is revealing, useful, and helpful to the client in successfully managing his or her weight state over time. The more knowledge and encouragement the client receives, the higher are the chances for success.

In a first embodiment of the sensor device 20, only one client can be served at a time. A second embodiment of the weight sensor device includes additional indicators 30B, each one being assigned to an individual in a small group by the professional manager through the system. These can either be identified by color or text, or can be a text or iconic display. The sensor device 20 is turned on with a first foot tap, or equivalent. A second, third, or a proper number of taps will cause the sensor device 20 to sequence to that specific indicator 30B assigned to a specific individual using the device at that time. The selection can also be accomplished through a communications device having a selection screen on which personalized identifiers, such as icons, appear, and pointing and clicking at the client's unique identifier. It could also be accomplished by typing in or speaking an identifier.

If a new weight recording should have been received according to the client's preselected weigh-in frequency, and none are found in the weight database, then a reminder may be automatically dispatched to the client. The algorithms 10B contain the rules, logic and intelligence of how, when, and if the messages are to be sent or not sent, modified, or manually created by the professional manager, and they will always comply to the rules specific to each client.

Thus, experience and research indicate that, in the preferred embodiment, a system that keeps a weight issue client in daily contact with a weight management professional manager, e.g., physicians, osteopaths, physician's assistants (PA's), chiropractors, nurse practitioners, dieticians, physical therapists, and physical training and/or conditioning instructors, is a powerful methodology for improving the chance of maintaining the client's reduced weight permanently. The daily contact can be performed indirectly through the use of technology that intelligently monitors the weight state of the client along with daily reports to the professional manager. If the client is conforming to his, or her, agreed upon regimen, the system provides guidance and advice electronically as appropriate. If the client is not conforming, then the system informs the professional manager, and a manual intercession is precipitated, usually in the form of an office visit. A significant portion of the overweight population now has the capability of improving the success number, which is associated with weight stability of approximately 11%-89% of the population returning to their original overweight condition within two years of having lost weight, to greater than 50%.

In the preferred embodiment, the system 10 is a server centric duplex (two-way) communication system that features daily weight monitoring by the professional manger, and that either automatically or manually, through electronic communication means, establishes a dialog between the manager and the client. The algorithms 10B automatically analyze each client's daily weight data along with certain client metrics, and, in turn, reports to the client and the manager, as appropriate. Further, the system is so designed that it is, at each client's option, ergonomically customized for that individual. Different personalities require different communication styles and interaction methods. Providing clients with their preferred styles and interaction methods improves, for a significant population of clients, mental comfort and therefore responsiveness, thereby improving the chances of a successful outcome.

In the preferred embodiment, the weight sensor device 20 can also be described as a weight transducer. A weight transducer is a device that converts pressure into an electronic signal which can be converted into weight data. The device 20 requires the client to stand on a surface that transfers all the weight driven energy of that person to the pressure transducer which, in turn, converts that energy into a weight variable electronic signal. Further, the device 20 contains circuitry that memorizes the weight data and, when queried, sends the weight data, either wirelessly or through a USB-wired connection, to a computer and/or a personal digital assistant. Purposely and fundamentally, the device 20 contains no weight measurement readout capability as would be included in a common household scale. The only feedback is an indication when the device is ready for a weight measurement, and then another indication that a successful measurement has occurred, and finally, another indication when that data has successfully been transmitted to the target computer and/or personal digital assistant. The weight transducer device 20 is placed in a location that is convenient for the client, such as in the client's bathroom, gym, workplace, etc, even in a hotel room when traveling. In other words, the location of the weight transducer device 20 is placed where it is most convenient for the client to use at the beginning of his or her metabolic day. A metabolic day begins after a normal evening sleep has ended, and the client has not consumed any food or liquid.

The system provides a menu of ergonomic styles that are built into the system and chosen by the manager in collaboration with the client. The choices are based on the specific needs and style that both agree will be best for the client. The system is unique because it provides, based on certain proprietary algorithms 10B, the means for tracking daily weight variations and trends considering a given client's history, metrics, and needs. The system provides the means for determining what is significantly happening to that client's weight before it would normally be noticed and/or responded to using the common established methods, along with a personalized daily report to the client and a daily status report to the manager. This occurs automatically with computed messages using one or a plurality of algorithms that utilize the client's database. Under certain circumstances, e.g., the client is not successfully responding to the agreed upon regimen and is beginning to regain lost weight, an alert is generated by the system and the manager intercedes by arranging an office visit. Such response and arrangements are easily and efficiently implemented by the system with little effort on the part of the manager or on his or her staff.

The greatest value for the client is that he or she is being monitored and managed by the manager on a daily basis. The client is never alone in this process. The communication and analytical process is automatic (and manual where appropriate), constant, and tailored for each client. An important rudiment of success for the system for each given client is the element of the communication style. This will always be his or her, preferred, most comfortable means of engagement. The personalized communication aids in overcoming the normal resistant factors of human behavior and departs from the common methods utilized by other systems that have been designed for the population at large. Daily contact, complete and current metrics, personalization, and convenience are the essential elements driving the instant invention.

By way of review, in the preferred embodiment, a potential client agrees to purchase and sign onto the system. The manager interviews the potential client and enters the required information directly into the terminal 34 or a satellite workstation or an ancillary limited satellite workstation, primarily only useful for enrollment purposes and connected to the satellite workstation through a local network, preferably a wired Ethernet connection as opposed to a wireless link because of security issues. A typical reason for using the ancillary workstation would be that the satellite workstation is in use by another person. At this point, the client must make a decision whether to choose a sixteen week program that consists of classes dedicated to program training, nutritional teaching, and weekly personal coaching, or a maintenance program, or both. Typically, a client will be engaged for a two year program.

Once a client has chosen an acceptable password, a "nickname", the program he wishes to participate in, and been assigned and received his personal code, the client is enrolled. The client is given the transducer device 20, a USB cable, and an initialization instruction sheet. The process begins by turning on the client's communications device, e.g., the computer 26, the telephone 24, or, as noted above, any equivalent device such as a smartphone, e.g., a BlackBerry (trademark) or an iPhone (trademark) device, preferably having a screen. The next step is going "on line" through the client's chosen browser and logging on to the system's website, where a home page has a window that reads, "Clients Initializing—for the first time or reinitializing—click here". The client proceeds by clicking that window. The first response will be a pop-up window that illustrates how to how to connect or associate the transducer device 20 to the client's communications device. The three options available are: direct cable connection using the USB cable (the connection is between a USB port on the transducer device 20 and a USB port on the communications device; BlueTooth wireless communication 7.x protocol or better (included in the transducer device 20);

and standard 2.4 GHz 802.11g wireless LAN protocol (included in the transducer device 20). The home page will further request that the client choose one of these options by clicking on the proper check box. Usually the choice will be discussed with the client at the enrollment process so that the client will have been briefed by the manager concerning what to do—ahead of time—thereby helping eliminate confusion on the part of a technically non-sophisticated person.

To turn the transducer device 20 on, the client merely taps it by hand or foot, looking for the red LED to come on. When it comes on, a red light in the pop-up window (connection window) will also come "on". At the bottom of the pop-up window, there will be a small window that will start flashing called "click here for next". A new pop-up security window will appear that will request the client's password and memorize the typed-in password, eliminating the need to enter it every time when logging into the system, or not memorize the password, thereby requiring the password to be entered every time one logs into the system. The security window will also request the client's nickname and personal code to be typed in. At the bottom of the security window, a Help Desk telephone number will appear that can be called at anytime to support the client at any point in the initialization procedure.

Upon successfully entering this data and receiving a success or failure message from the system, another set of simple instructions will appear. These instructions will lead the client through a process for testing that the transducer device 20 is working properly and communicating with the client's communications device, as well as that the client's communications device is also working properly and communicating with the system. If the process is successful, then a success or failure message will appear on the client's PDA or equivalent. If not, the message will request that the client repeat the process or call the Help Desk.

Once the test has been successfully completed, a small window titled "click here for next step" will begin flashing. This will activate another pop-up window that will request that the client is to step on to the transducer device 20. The transducer device 20 should be on a hard surface as opposed to a carpeted surface. The client should remain on the transducer device 20 until the transducer device 20 LED turns green. At this point, the client's PDA or equivalent will display a success message "You have successfully set up your system. Thank You!" The client is now ready to begin the program which will start at the beginning of the client's next metabolic day.

At the beginning of each metabolic day, the client proceeds through the following routine: The client turns on the communications device, and clicks a personal icon that includes that client's nickname located on the screen. Other icons for other persons sharing the same transducer device 20 may appear on the screen. Each icon will have a different "nickname" embedded in it, and therefore be associated with a different personal code and password. A window opens requesting that client's password or, if the client opted to have the password memorized, this step is bypassed. Either way, an on-line start is initiated, followed by a connection with the system and the display of a message entitled "System Connected". A session window for that client opens, and the weighing process begins. The session window displays a date, time, and time zone. Further, the process is illustrated by a graphic displaying all the connections and a message entitled "The system is ready". Before eating or drinking anything, the client first taps the device 20 with his foot, looking for the red LED to turn on. This could be replaced or accompanied by an auditory beep. If the first tap is unsuccessful, the client is instructed to tap again. If there is no success, the client is instructed to call the Help Desk. When the red LED is on, the device is going through the process of connecting with the PDA or equivalent. When the red LED turns green, the system is ready for the client to step on the device 20 and be weighed. The green LED will start blinking when a successful measurement has been made and successfully received by the PDA or equivalent. The blinking will continue until the client steps off the device 20. When the blinking stops, the device 20 will automatically turn off. The session window will remain on until the weighing data has been successfully received by the system, and a success message will appear on the session window of the PDA or equivalent. The success message will remain until the client clicks an "end session" box.

Depending on what periodicity and styles that were chosen by the client during enrollment, the periodic report will be generated in an email to the client. The report will appear as a flagged intrusion in his chosen email address(es) and the client clicks a received box. The report can only be generated after the manager has reviewed the daily report. The periodicity can be weekly, bi-weekly, monthly, bi-monthly, etc. The weighing schedule can be daily, bi-daily, weekly, bi-weekly, etc. The style can be a digital or analog readout, color indicators, auditory indications such as music or sounds, icons and graphs.

From the manager's perspective, each metabolic day consists of members of the group that he or she is managing, and of executing their individual weighing sessions. Obviously, some clients will always respond and others will not. The system must tolerate both situations and record what did and what did not occur. As a result of a successful weighing session, data is sent to a central server of the system 10. Assuming that the data has been successfully sent, and thus there was no failure message causing the weighing session to be repeated or a call to the Help desk, the data—for each individual—is processed and put in its proper file and associated batch. Batches are groups associated with a given manager. Each manager has his own assigned client batch file that is only available to that manager or his appointed surrogates. The processed data from each of the clients is accumulated in a batch queue until the established daily cut-off time has occurred, e.g., 12:00 pm. After the cut-off time has passed, weighing sessions are no longer accepted for that metabolic day. New weighing sessions can only occur on the next metabolic day that is consistent with each client's chosen weighing schedule. Should a client attempt a second, or multiple sessions, on any given metabolic day after a successful session has occurred, it will be rejected, and the client will be informed that a successful session has already occurred. Those clients who did not attend their weighing session are recorded as absent, and a message is sent with the periodic report noting same.

A client's metabolic day always begins when he has finished sleeping and has not had anything to eat or drink and has executed a weighing session. When the client enrolled into the system, he was instructed that the time for the periodic weighing session could not begin before 12:00 am on any given metabolic day and will always end before 12:00 pm on that same day. After the cut-off time has passed, the central server generates a report (see FIG. 3) to each manager with all details regarding his or her group (batch).

Each bar in FIG. 3 represents a client. The number below each bar is that client's file number for a given manager. By pointing the cursor over each client number (#) and clicking, the name of that client will pop-up in a small window for convenient identification. The green portion of a given bar represents the client's weight for the reported weighing session, and the color green represents that the client is in the manager's established safe zone for that client's weight. The "weight zones"—green, yellow, and red—for each client is established by the manager after a successful enrollment has occurred. The system contains templates that suggest weight zone metrics to aid the manager with this task. The yellow portion of the bar, if it is present, is an indication of a cautionary weight gain. The red portion of the bar, if it is present, is a significant weight gain that creates a "red alert". By pointing the cursor and clicking on any portion of a given bar, a complete view of a given client's file can be examined, as well as printed out, and sent to a third party, provided the manager and his associates have the right to view the file. Within each manager's domain, an "entry key" will be assigned by the system to the manager for system access. Therefore, the given manager will be responsible for all security issues within his or her domain.

The green bars automatically, through the central server, create messages that are sent to each client in the preferred style. The yellow bars also automatically do the same unless the manager chooses to override the automation and send his own manually created message. The red bars offer no automation and must be manually responded to and created by the manager. In most cases, it will be setting up an office visit.

After the metabolic day cut-off time has passed, the manager reviews the cockpit view of FIG. 3 and clicks on the "reviewed" box. This initiates sending the "reviewed" signal to the central server. Having received the "review" signal, the central server sends all automatic reports to all clients of a given group batch in each client's appropriate report period and style. A "reports sent" message is sent back to the manager with a time stamp. Before the beginning of the next metabolic day, all client reports will be available containing all report details and an acknowledgment of reception by each client. The optional yellow manual messages and the required "red alert" messages are to be sent as a separate batch once the manager has reviewed each relevant client file. These messages also require a report and acknowledgment. When a client visits the manager, the manager might want to reset the client's weight zones (green—yellow—red). This is done by opening the client's file and changing the numbers.

When a manager agrees to sign onto the system, the manager must be enrolled. An engagement form is used for gathering information required that will be ultimately be entered online. Further, the manager will receive an engagement contract, which describes all the obligations, responsibilities, limitations, and liabilities of the participating manager and the system operator. When the manager has satisfactorily reviewed and executed the engagement contract, the information from the engagement form is entered online into the central server, and a unique entry key that provide access to the system is assigned.

The system 10 or central server preferably comprises a main or central server, a proxy server, a terminal server, and a database. The main server performs all computational functions. The database stores all client files. The proxy server is a "go-between" for all computational requests, dispatches and reports, and serves as an anonymity wall for security issues. The terminal server manages and combines all the communication channels, which are bidirectional and connect the main server to all clients and all managers. Both physical and virtual resources are provided through the terminal server by providing the benefits of a virtual operating system to all end users through the Internet.

The system 10 or central server preferably further comprises firewalls, routers, executive workstations and auxiliary workstations. Firewalls are for blocking all unauthorized access to the system while, at the same time, granting authorized access. Routers link multiple networks together, thereby providing universal access through the Internet to all clients and managers to the central server. The executive workstations and auxiliary workstations are high-end computers used for entering, monitoring, testing and managing all system software and its functions. They have the ability to manipulate and navigate each and all aspects of the system. The executive workstations are connected to the central server through the Internet. The auxiliary workstations are connected to the central server through the Ethernet. Since the latter are hardwired to the central server, they must be physically very close. The auxiliary workstations are mostly setup and emergency tools under lock and key, or are portable and brought to the central server only when needed.

It will be understood that each of the elements described above, or two or more together, also may find a useful application in other types of constructions differing from the types described above.

While the invention has been illustrated and described as a weight management system and method using a weight sensor device with a zero-readout, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

We claim:

1. A system for managing body weights of multiple human users, comprising:
a controller for recording personal data for, and for communicating with, each user, the personal data including identification data for uniquely identifying each user to the controller, and communications preference data for specifying how each user wishes to be communicated with by the controller; and
an actuatable weight sensor device in bidirectional communication with, and located remotely from, the controller, the weight sensor device having a platform on which a user stands during weighing, and a load cell operatively connected to the platform for generating, and sending to the controller, an electrical weight signal indicative of the body weight of the standing user, the weight sensor device being actuated and operated by the standing user who is identified to the controller by the identification data, the weight sensor device itself providing no indication to the standing user of the standing user's body weight,
wherein the controller processes the weight signal received from the weight sensor device, and sends a body weight status communication to each user in accordance with the communications preference data specified by each user.

2. The system of claim 1, and further comprising a manager terminal operatively connected to the controller for inputting the personal data to be recorded to the controller, the personal data including human metrics data unique to each user.

3. The system of claim 2, wherein the manager terminal is operated by a human weight manager to supervise the multiple users, wherein the controller has a database customized for each user, and wherein the manager terminal includes a display for displaying each user's body weight status.

4. The system of claim 1, and further comprising a communications device operated by each user, and wherein the controller sends the body weight status communication via one of a wireless and a wired link to the communications device.

5. The system of claim 4, wherein the communications device is a handheld telephone operated by a respective user.

6. The system of claim 1, wherein the weight sensor device has an indicator for indicating when the weight sensor device is ready to measure the standing user's body weight, and when the standing user's body weight has been successfully measured.

7. The system of claim 1, wherein the weight sensor device is associated with a group of the users, and has a display that displays a plurality of identifiers, one for each user.

8. The system of claim 1, wherein the weight sensor device is associated with a group of the users; and further comprising a communications device operated by each user, and having a display that displays a plurality of identifiers, one for each user.

9. A method of managing body weights of multiple human users, comprising:
recording personal data for each user in a controller operative for communicating with each user, the personal data including identification data for uniquely identifying each user to the controller, and communications preference data for specifying how each user wishes to be communicated with by the controller;
weighing each user by having each user stand on a platform of an actuatable weight sensor device having a load cell that generates an electrical weight signal indicative of the body weight of the standing user during weighing, the weight sensor device being actuated and operated by the standing user who is identified to the controller by the identification data, the weight sensor device itself providing no indication to the standing user of the standing user's body weight;
sending the weight signal for processing to the controller located remotely from the weight sensor device;
processing the weight signal received from the weight sensor device; and
sending a body weight status communication to each user in accordance with the communications preference data specified by each user.

10. The method of claim 9, and further comprising inputting the personal data to be recorded to the controller with a manager terminal, the personal data including human metrics data unique to each user.

11. The method of claim 10 and further comprising supervising the multiple users by a human weight manager operating the manager terminal, customizing a database for each user, and displaying each user's body weight status on the manager terminal.

12. The method of claim 9, and further comprising instructing each user to operate a communications device, and wherein the body weight status communication is sent via one of a wireless and a wired link to the communications device.

13. The method of claim 12, wherein the communications device is a handheld telephone.

14. The method of claim 9, and further comprising indicating on the weight sensor device when the weight sensor device is ready to measure the standing user's body weight, and when the standing user's body weight has been successfully measured.

15. The method of claim 9, and further comprising associating the weight sensor device with a group of the users, and displaying a plurality of identifiers, one for each user, on the weight sensor device.

16. The method of claim 9, and further comprising associating the weight sensor device with a group of the users, instructing each user to operate a communications device, and displaying a plurality of identifiers, one for each user, on the communications device.

17. The method of claim 9, wherein the weighing is performed periodically.

* * * * *